(12) United States Patent
Stelzer (10) Patent No.: US 8,970,950 B2
(45) Date of Patent: Mar. 3, 2015

(54) SINGLE PLANE ILLUMINATION MICROSCOPE

(75) Inventor: Ernst H. K. Stelzer, Meckesheim (DE)

(73) Assignee: Europaeisches Laboratorium fuer Molekularbiologie (Embl), Heidelberg (DE)

( * ) Notice: Subject to any disclaimer, the term of this patent is extended or adjusted under 35 U.S.C. 154(b) by 1109 days.

(21) Appl. No.: 11/592,331

(22) Filed: Nov. 3, 2006

(65) Prior Publication Data

US 2007/0109633 A1 May 17, 2007

Related U.S. Application Data

(63) Continuation-in-part of application No. 10/538,081, filed as application No. PCT/EP03/05991 on Jun. 6, 2003.

(30) Foreign Application Priority Data

Dec. 9, 2002 (DE) .................................. 102 57 423

(51) Int. Cl.
*G02B 21/06* (2006.01)
*G01N 21/64* (2006.01)
(Continued)

(52) U.S. Cl.
CPC ............ *G02B 21/06* (2013.01); *G01N 21/6458* (2013.01); *G01N 21/4795* (2013.01); *G02B 21/0032* (2013.01); *G02B 21/0076* (2013.01); *G02B 21/16* (2013.01); *G02B 21/367* (2013.01)
USPC ....................................................... 359/385

(58) Field of Classification Search
CPC ........ G02B 21/06; G02B 21/30; G02B 21/34; G02B 21/24; G02B 21/26; G02B 21/22; G02B 21/14; G02B 21/006; G02B 21/18; G02B 21/20

USPC .......................................... 359/368, 385, 398
See application file for complete search history.

(56) References Cited

U.S. PATENT DOCUMENTS 5,570,228 A 10/1996 Greenberg
5,710,625 A 1/1998 Neumann et al.
(Continued)

FOREIGN PATENT DOCUMENTS

JP 39-38343 12/1939
JP 2010230 A 1/1990
(Continued)

OTHER PUBLICATIONS

Cole et al., Time-domain whole-field fluorescence lifetime imaging with optical sectioning, Journal of Microscopy, vol. 203, Pt 3, Sep. 2001, pp. 246-257 (henceforth Cole).*

(Continued)

*Primary Examiner* — Thomas K Pham
*Assistant Examiner* — Jie Lei
(74) *Attorney, Agent, or Firm* — Rothwell, Figg, Ernst & Manbeck (57) ABSTRACT

The invention relates to a microscope in which a layer of the sample is illuminated by a plurality of thin strips of light (11) passed through a grid (34) and the sample is viewed (5) perpendicular to the plane of the strips of light. To record the image, the object (4) is displaced through the strips of light (11). At least three different images of the objects (4) are made at different phase angles. The images can be combined to form a single combined image.

27 Claims, 6 Drawing Sheets

(51) Int. Cl.
   *G01N 21/47*   (2006.01)
   *G02B 21/00*   (2006.01)
   *G02B 21/16*   (2006.01)
   *G02B 21/36*   (2006.01)

(56) References Cited

U.S. PATENT DOCUMENTS

| | | |
|---|---|---|
| 5,903,781 A | 5/1999 | Huber |
| 7,218,393 B2 | 5/2007 | Sharpe et al. |
| 2007/0171519 A1* | 7/2007 | Wolleschensky ............. 359/385 |

FOREIGN PATENT DOCUMENTS

| | | |
|---|---|---|
| JP | 2239642 A | 9/1990 |
| JP | 4127152 A | 4/1992 |
| JP | 7174687 A | 7/1995 |
| JP | 07253309 | 10/1995 |
| JP | 08271225 | 10/1996 |
| JP | 8-327947 A | 12/1996 |
| JP | 2004531729 A | 10/2004 |
| WO | WO 02/095476 A2 | 11/2002 |

OTHER PUBLICATIONS

Arne H. Voie, "Imaging the intact guinea pig tympanic bulla by orthogonal-plane fluorescence optical sectioning microscopy", Hearing Research, 171 (2002), pp. 119-128.

Voie et al., "Orthogonal-plane fluorescence optical sectioning: three-dimensional imaging of macroscopic biological specimens", Journal of Microscopy, vol. 170, pt. 3, Jun. 1993, pp. 229-236.

Voie et al., "Three-Dimensional Reconstruction of the Cochlea from Two-Dimensional Images of Optical Sections", Computerized Medical Imaging and Graphics, vol. 19, No. 5, pp. 377-384, (1995).

European Official Action for European Patent Application No. 03 732 549.5-1524, dated Mar. 12, 2010, 4 pages.

English Language Translation of European Official Action for European Patent Application No. 03 732 549.5-1524, dated Mar. 12, 2010, 3 pages.

\* cited by examiner

SINGLE PLANE ILLUMINATION MICROSCOPE

REFERENCE TO PREVIOUS APPLICATIONS

This application is a Continuation-in-Part of Ser. No. 10/538,081, Jun. 9, 2005 which is a national tease of PCT/EP03/005991 filed on Jun. 6, 2003 and claims priority to German Patent Application No. 10257423.5 filed on Dec. 9, 2002.

FIELD OF THE INVENTION

The present invention relates to a microscope suitable for the high resolution, three-dimensional viewing of millimeter-sized biological objects.

BACKGROUND TO THE INVENTION

In contrast to work on single cells, light microscopy studies on embryos and other samples relevant to developmental biology suffer from the particular problems of absorption and resolution loss. For example, biological questions relating to gene expression patterns in developing organisms can currently be answered only with difficulty by light microscopy imaging methods, since they are often too slow, too weakly resolving or technically complex, or they do not allow millimeter-size objects to be viewed with a sufficiently high free working distance or inside a sample holder. An acceptable solution must allow the handling of large samples and rapid high-resolution acquisition of the data, while being technically as simple as possible to implement.

The scientific literature discloses a microscope for oceanographic research, which is characterized in that it produces an illumination light plane in a sample chamber by using a laser and detects the fluorescent signals produced in the illumination light plane perpendicularly to this plane by using a camera [E. Fuchs et al., Opt. Express 10, 145 (2002)]. This microscope (as well as others published in the scientific literature) is similar to the ultramicroscope of H. Siedentopf and R. Zsigmondy [Ann. Phys. 10(4), 1 (1903)] and is used for the detection of individual free-floating particles such as bacteria. It is not suitable for recording millimeter-size samples, for example in developmental biology, since a cuvette is used as the sample holder. It is likewise unsuitable for three-dimensional imaging, since it does not have any means of moving the sample relative to the illumination light plane.

German Patent Application No. DE 19720513 A1 or U.S. Pat. No. 5,903,781 and the scientific literature [D. Huber et al., J. Microsc. 202, 208 (2001)] disclose an instrument for three-dimensional macrography, in which an arrangement for producing light planes is used for the photographic recording of objects. In this case, an object is moved through an illumination plane and the reflected and scattered light is detected by a camera. This equipment is used to prepare three-dimensional reconstructions of centimeter-size objects. It is not, however, suitable for the use of fluorescent signals or for the high-resolution rendition of objects. A slit pattern diaphragm in conjunction with a mirror arrangement is used for producing the light planes. Owing to the use of an only linearly mobile sample stage, the sample cannot be rotated so that it is not possible to view the sample from several sides.

The technical scientific literature furthermore discloses constructions for optical tomography. Optical projection tomography is used, for example, in gene expression analysis [J. Sharpe et al., Science 296, 541 (2002)]. This is a system in which projections of biological samples are recorded, the sample being rotated about an axis perpendicular to the detection direction. Since the sample is not selectively illuminated perpendicularly to the detection axis by an illumination light plane, in contrast to the microscope according to the invention, the microscope has a very long depth of focus with which a large part of the sample can be acquired. The microscope does not therefore offer the opportunity to move the sample along the detection axis in order to record a three-dimensional image. A three-dimensional image of the sample with spatial resolution is therefore possible only by reconstruction from the projections.

German Patent No DE 43 26 473 C2 discloses a confocal theta microscope, which is characterized in that it uses a first objective for point illumination and a second objective to project the object light onto a point detector, the detection direction being substantially perpendicular to the illumination direction. The confocal overlap region of the illumination volume with the detection volume is therefore particularly small, and the microscope achieves an almost isotropic resolution whose order of magnitude corresponds to the lateral resolution of a confocal microscope.

This theta microscope is arranged confocally, however, which places stringent requirements on the relative alignment of the illumination and detection focal points. Despite a large working distance, it is furthermore not readily capable of imaging large objects. This is because the object in the theta microscope does not have enough freedom of movement for scanning the object, and owing to the point detection it has to be scanned in three directions so that imaging takes a very long time. The illumination light is focused at an illumination point.

The concept of structured illumination of the object was introduced to wide-field fluorescent microscopes as a means to discriminate against out-of-focus light (see e.g. Neil M A A, Squire A, Juskaitis R, Bastiaens P. I. H, Wilson T, J. Microsc. 197-201 (2000). This requires the recording of at least three individual images in which a symmetric pattern is displaced by 120° and 240°. The root of the sum of the three squared difference images is calculated to obtain a resultant image in which those contributions of the individual images which contain no spatially-relevant information are eliminated. The resultant image features have an improved contrast and an improved resolution.

SUMMARY OF THE INVENTION

It is an object of the present invention to provide an improved microscope.

It is furthermore an object of the present invention to improve the contrast and resolution of a microscope suitable for the high-resolution three-dimensional viewing of millimeter-sized biological objects.

These and other objects of the invention are achieved by providing the microscope with a focusing arrangement which produces a two-dimensional object illumination pattern extending in the direction of an illumination axis of the illumination beam path and transversely thereto. The detection direction of a detection beam path is substantially orthogonal to the two-dimensional object illumination region. A mobile arrangement is provided for producing a relative movement between the two-dimensional object illumination region and an object to be studied.

The two-dimensional object illumination pattern extends in the direction of an illumination axis of the illumination beam path and perpendicular thereto, in particular substantially perpendicular to the axis of the detection beam path.

It should be noted that the detection direction of the detection beam path is substantially orthogonal to the two-dimension object illumination region. However, the advantages of the invention are also achieved when the angle is close to a right angle, but not exactly a right angle.

In the embodiment of the invention, the mobile arrangement allows the scanning of the two-dimensional object illumination pattern over the object to be studied. This has the advantage that only narrow regions of the object are illuminated at any one time. Fluorescence in the neighboring regions does not therefore intrude into the illuminated region and as a result does not affect the image being made of the illuminated region.

The two-dimensional object illumination pattern is preferably a set of substantially parallel light stripes. The term "two-dimensional" in this example thus refers to a physical two-dimensional set of substantially parallel light strips. The light stripes are shifted with respect to the object to be studied so that the area of interest of the object can be progressively illuminated. The images made from the same narrow regions of the object can be combined to produce a resultant image which is of high resolution.

Preferably light stripes are generated by a grid from a single light source. This ensures that the light in the light stripes are in phase with each other.

The mobile arrangement can produce a rotational movement or displacement movement of the object to allow the object to be viewed from a plurality of directions.

In one embodiment of the invention the illumination beam path has a cylindrical lens for focusing the illumination light. The cylindrical lens is movable with respect to the illumination axis and can also be rotated or tilted about the illumination axis. It would, of course, be possible to use other focusing elements, such as a holographic element or a conical lens (axicon) or a phase plate or other elements for producing a Bessel beam.

In a preferred embodiment of the invention, the mobile arrangement comprises at least one light mirror which is driven by a motor (including a galvanometer). In conjunction with an imaging lens (e.g. an f-Theta lens) this replaces a cylindrical lens and is used to form the light sheet. It is advantageous as there is more control over the light sheet. It is also advantageous since it requires optical elements that are easier to produce. The length of time at which the light sheet illuminates the sample at various positions can be easily varied. As a result, regions of interest of the sample can be scanned for different periods of time and also the intensity of the light sheet can be changed as a function of beam location by changing the intensity of the light source. It would also be possible to use two light mirrors to adjust the creation of the light sheet more accurately. Furthermore the location and the orientation of the light sheet can be adapted by varying the direction of movement of a light mirror which allows the taking into account of the shape or other properties of the sample. The size of the light sheet is more easily adjusted which can result in energy savings and furthermore, there is little loss of energy at the light field of view spatial filter. This can allow, at least in principle, the use of a weaker laser as the light source whilst still maintaining the quality of the image.

Scattered light or fluorescent light of one or more wavelengths is used in the microscope. The light source is a lamp or a laser which provides light of one or more wavelengths. Preferably a laser is used as this has highly coherent light.

In an advantageous embodiment of the invention, at least two illumination beam paths with essentially opposite illumination directions are provided. The at least two illumination beam paths produce locally overlapping two-dimensional object illumination patterns.

The detection is preferably carried out using a two-dimensional detector which detects the full field, for example a CCD camera. When such a detector is used, rapid imaging is possible and the movement of the sample for a three-dimensional exposure is limited to one direction (i.e. along the detection axis). The resolution of the system is determined by the lateral resolution of the detection optics.

Since the surface area of currently available detectors is generally insufficient to guarantee complete high-resolution recording of objects measuring several millimeters, in one embodiment of the microscope according to the invention it is possible to move the detector in the detection plane, i.e. essentially laterally with respect to the detection direction in order to record images of parts of the object, which can be combined to form an image of the entire object.

In a simple preferred structure, no optical elements are used for guiding the beam paths. Mirrors, dichroic mirrors, beam splitters or optical fibers, for example, may nevertheless be used for guiding the beam paths. The fact that the illumination and detection beam paths are separate in the microscope according to the invention makes it possible to obviate the use of passive components such as dichroic mirrors or active, for example acousto-optical components for separating the illumination and fluorescent light, as is customary in other fluorescence microscopes.

The structure may, for example, be supplemented with a further illumination light path, the light of which is focused to form a strip, or object illumination region, which preferably lies in the same plane as the object illumination region of the first illumination light path, so that better lighting of the sample is achieved. The light for this further illumination light path may come from the same light source. In this case, the sample is preferably illuminated from two opposite directions. The alignment workload in the microscope according to the invention is small in contrast to 4Pi confocal microscopy [S. Hell and E. H. K. Stelzer, J. Opt. Soc. Am., A 9, 2159 (1992)] since it is only necessary to superimpose two light strips which are several micrometers thick. Furthermore, the phase of the beams does not need to be taken into account.

The microscope according to the invention may nevertheless be operated as a non-confocal 4Pi theta microscope. In this case, as in a 4Pi(A) confocal microscope, the sample is illuminated coherently from two opposite directions so that an interference pattern which spatially modulates the intensity in the illumination light plane occurs along this illumination axis. The illumination volume is thereby halved, and by displacing the interference pattern (by adjusting the phase difference between the beams) it is possible to illuminate complementary regions of the sample so that an image can be reconstructed with increased resolution along the illumination axis.

The structure may be supplemented with a further detection light path, for example, by which light emitted in the opposite direction to the existing detection light path is detected. In this way, detection of the light can always take place so that the light travels as short as possible a path through the sample.

Scattered light detectors and/or transmission light detectors may additionally be provided.

Although it is possible to place the sample on a sample stage or hold it in air in the microscope according to the invention, the sample is preferably held from above by a holder in a water-filled sample chamber and can be rotated about the vertical axis, i.e. the axis in the gravitational direction. This has the advantage that there is no change in the gravity acting on the sample, and it is not deformed, when the sample is rotated for imaging from another direction. During such a rotation of the sample in the sample chamber, the sample chamber is preferably not moved so that the optical path lengths (apart from differences due to the refractive index in the sample itself) do not change during the movement process. This leads to a better image quality. The sample held in this way may advantageously be oriented so as to minimize the effect of strongly scattering or absorbing parts of the sample during the image recording.

In another embodiment of the microscope according to the invention, it is also possible to rotate the illumination and detection paths about the object to be studied while the latter is stationary. Then, however, the sample or object generally needs to be readjusted in order to be recorded in further images.

The object to be studied lies in the two-dimensional object illumination region when an image is recorded, the object being substantially larger than the thickness of this region. A two-dimensional image of the object parts located in this region is recorded by the two-dimensional detector. A three-dimensional image of the object is recorded by scanning the object in the detection direction through the stationary illumination region (or by scanning the illumination region through the object), a two-dimensional image being recorded in each position of the object. The synchronization of movement, illumination and detection is preferably optimized in order to minimize the stress on the sample.

The rotation of the object (like the linear scan movement) is preferably controlled electronically, so that the recording of a plurality of images from different angles can be automated and the speed of the sample examination can be increased. The number of images and the rotation angles of the sample which are required for recording a full image with a particular spatial resolution may be optimized in favor of a short sample examination time and therefore low stress on the sample.

Preferably, the object to be studied can also be tilted about the illumination axis so that it can also be viewed from additional directions. In another embodiment of the microscope according to the invention, a second detection light path is provided which makes it possible to detect the light emitted downward. If the object illumination region is then rotated by 90 degrees about the illumination axis (for example by rotating the cylindrical lens), then the sample can be optically sectioned horizontally (and a three-dimensional image can be produced by a vertical scan movement).

Advantageously, in the microscope according to the invention, the cylindrical lens can preferably be moved with a high frequency, for example moved in the illumination light path with a high frequency along the cylinder axis and/or the illumination axis, and/or the cylinder axis can be inclined with a high frequency in the direction of the illumination axis, so that the effect of contamination on the cylindrical lens or a low optical quality of the cylindrical lens is less strong and the sample is lit more uniformly.

Preferably, a plurality of biological samples can be held simply by being embedded in a gel (about 99% water) or another polymerizing or crosslinking structure. One non-limiting example of a gel used is agarose gel.

The images recorded from different directions by rotating the object to be studied allow its three-dimensional reconstruction by combining the individual three-dimensional raw data records. Since only a part of the sample is imaged optimally in the preferred embodiment of the microscope according to the invention (in general the two octants which lie inside the right angle between the illumination and detection axes), at least four images are required for good reconstruction of the full sample. These images can be combined so that the reconstruction offers a higher resolution than the individual images. The quality of the reconstructed image can be improved by recording along further angles, so that the dead angles of the common optical transfer function are filled in.

When objectives with long focal lengths are used, a working distance of several millimeters is available. The size of the object is primarily limited by its optical transparency: if the entire object is intended to be studied (and not just the peripheral layers), enough light from every part of it must reach the detector in the one or other orientation.

As mentioned above, depending on the magnification of the optical system in the detection beam path, it may be necessary to displace the detector assigned to the detection beam path in order to be able to record a full image of the object to be studied, essentially owing to the limited number of detector pixels in two-dimensional pixel detectors. This means that the resolution of the overall system is essentially limited not by the numerical aperture of the optical components, in particular the lenses being used and therefore the resolution in the sample itself, but rather by the technical limitations which are encountered in the field of pixel detectors such as those used, for example, in CCD cameras. This problem may be countered by using high-resolution pixel detectors with a pixel number in the range of several millions as those used, for example, in astronomy or digital photography. These pixel detectors, however, are comparatively expensive and slow.

Another aspect of the present invention therefore relates to a microscope having at least one illumination beam path and at least one detection beam path, which is characterized in that each illumination beam path is provided with a focusing arrangement for producing a linear object illumination region which extends in the direction of an illumination axis of the illumination beam path, in that a detection direction of the at least one detection beam path is approximately orthogonal to the linear object illumination region, and in that at least one mobile arrangement is provided for producing a relative movement between the linear object illumination region and an object to be studied.

According to this aspect of the present invention, the object illumination region is therefore essentially limited to one dimension, i.e. the longitudinal dimension, so as to change over from the two-dimensional structure of the object illumination region as discussed above to an elongated or linear structure. With this linear object illumination region, accordingly, only linear sections of an object to be studied are lit and stimulated to fluoresce, or used to scatter light. These linear illuminated regions which are now produced can be imaged through the detection beam path or paths onto pixel detectors which have an elongated structure, i.e. pixels successively arranged essentially in one dimension. Such detectors, which are to be interpreted in principle as "one-dimensional" pixel detectors, can be obtained with a substantially larger number of pixels, for example up to 8000 pixels. The sections of an object to be studied which are now lit by the linear object illumination region and imaged in the detector can therefore be recorded with a correspondingly high resolution actually in the detector itself and can be converted into high-resolution images. Since the dimension of the pixels present in such pixel detectors, transversely to the longitudinal extent of the pixel detector, is generally much smaller than the width of the image of the linear object illumination region in this direction, even when taking into account the magnification produced in the detection beam path, it may be preferable to change over to elongated "two-dimensional" pixel detectors which, for example, have a pixel number of 64×4096, i.e. a substantially larger pixel number in the longitudinal direction of the object illumination region, or the corresponding image thereof, than transversely thereto.

In order then to be able to fully image an object to be studied with such a system, or to be able to produce a complete image of it, scanning may be carried out between the object to be studied and the illumination beam path or the detection beam path so that, in principle, the object to be studied is linearly sampled and the individual line images thereby produced can then be combined to form a full image.

In order to facilitate this, for example, the at least one mobile arrangement may be designed to produce a relative movement between the object and the linear object illumination region essentially orthogonally to the illumination axis and the detection direction. To this end, for example, the at least one mobile arrangement may be designed to move the object so as to produce a relative movement.

Alternatively or in addition to this displacement of the object to be studied, the at least one mobile arrangement may be designed to move the at least one illumination beam path at least in the linear object illumination region provided by it, in order to produce the relative movement. Since the object illumination region is in this case shifted while the object is stationary, for example, it is then necessary for the at least one mobile arrangement to be designed to move the at least one detection beam path in accordance with the movement of the at least one illumination beam path, at least in its region near the object.

As mentioned above, the at least one detection beam path may have a detector with a multiplicity of detector pixels, in which case it may be preferable to select the number and positioning of the detector pixels of the detector so that the at least one detection beam path projects a section of the object, illuminated by the at least one illumination beam path in the object illumination region, essentially fully onto the detector.

In order to be able to produce not only a surface image of an object to be studied with the system according to the invention, but also to be able to image it three-dimensionally by three-dimensional sampling, it is furthermore proposed for the at least one mobile arrangement to be designed to move the object to be studied, essentially in the direction of the detection direction of the at least one detection beam path.

From the explanations above, it is clear that an essential principle of the present invention is to produce an elongated object illumination region with at least one illumination beam path, in which an object to be studied can then be positioned in order to produce an image of the section of the object to be studied positioned in the object illumination region, or optionally the entire object, by stimulating fluorescence or by generating scattered light in at least one detection beam path.

The present invention therefore also relates to a microscope which has at least one illumination beam path and at least one detection beam path, and is characterized in that each illumination beam path is provided with a focusing arrangement for producing an object illumination region which extends in the direction of an illumination axis of the illumination beam path, in that a detection device of the at least one detection beam path is approximately orthogonal to the object illumination region, and in that a mobile arrangement is provided for producing a relative movement between the object illumination region and an object to be studied.

DETAILED DESCRIPTION OF THE INVENTION

Figure 1:
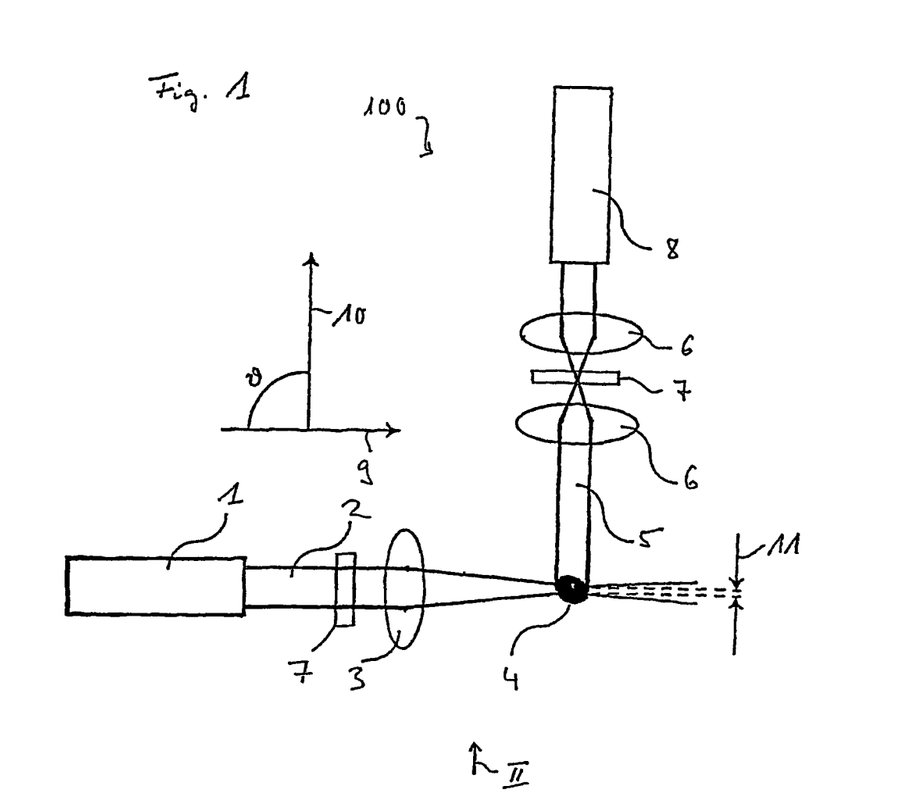
FIG. 1 shows the schematic representation of the beam path in one embodiment of the microscope according to the invention from the observation direction I of FIG. 2.

FIG. 1 shows an embodiment of a microscope 100 according to the invention. The embodiment comprises a light source 1, a collimated light beam 2 from which is focused into a sample 4 by a cylindrical lens 3. The cylindrical lens 3 creates a thin vertical light strip 11 by which fluorescent emission can be induced in the sample 4. Fluorescent light in a detection beam path 5 is projected through detection optics 6 onto a two-dimensional detector 8. The two dimensional detector 8 can be, for example, a CCD camera.

The structure is particularly simple owing to the substantially right-angled arrangement (=90 degrees) of an illumination direction 9 and a detection direction 10. In particular, the use of dichroic mirrors for separating illumination light from the light source and fluorescent light from the sample 4 in the detection beam path 5 can be obviated. Filters 7 in the illumination beam path 2 and in the detection beam path 5 are glass filters or acousto-/electro-/magneto-optical filters, and allow selective choice of wavelengths for the illumination of the sample 4 and the detection of fluorescent light emitted from the sample 4.

The sample 4 is held in a sample chamber 13 by a holder 12, and is moved through the stationary light plane 11 in the detection direction 10 for imaging. The holder 12 also makes it possible to rotate the sample 4 about a vertical axis 14, so that the sample 4 can be illuminated and viewed from several sides.

Figure 3:
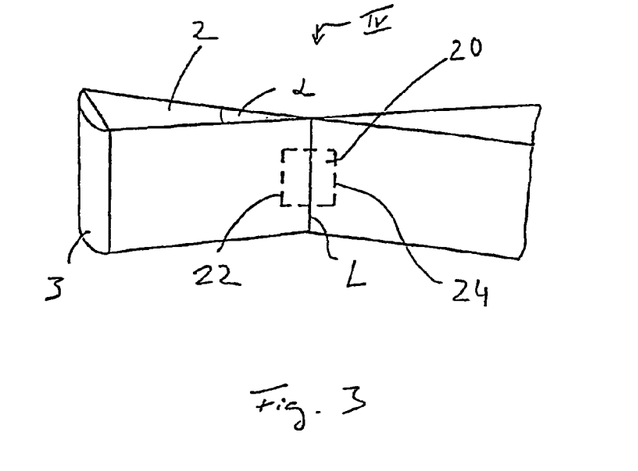
FIG. 3 shows an outline representation of the illumination beam path emerging from a cylindrical lens and forming an object illumination region in the region of a focus line.
Figure 4:
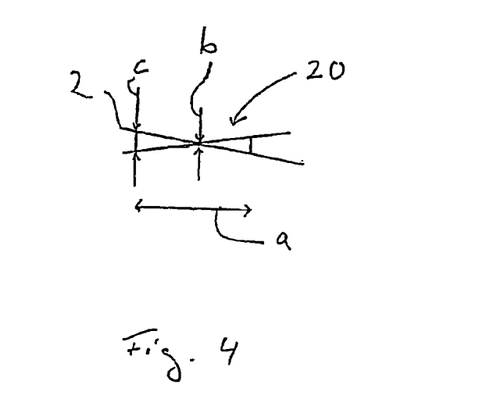
FIG. 4 shows a plan view of the beam path of FIG. 3 in observation direction IV in FIG. 3.

FIGS. 3 and 4 show in outline the aforementioned illumination beam path 2 which is produced with the aid of the cylindrical lens 3. Using the cylindrical lens 3, whose focal length may preferably lie in the range of from 10 mm to 100 mm, light emitted by the light source 1 is focused at a comparatively small angle α. In the region of a focus line L, this creates an object illumination region 20 indicated by the dashed rectangle in FIG. 3. The object illumination region 20 has a substantially two-dimensional or flat structure and is formed by cylinder sections on either side of the focus line L. With a dimension a of about 5 mm for this object illumination region 20 as measured in the direction of the illumination axis, or illumination direction, and with a thickness dimension of about 20 micrometers for the illumination beam path 2 in the region of the focus line b, a thickness dimension c of approximately 60 micrometers is obtained at the end regions 22, 24 of the object illumination region 20 lying in the illumination direction, although this naturally depends on the numerical aperture provided for the cylindrical lens 3. Throughout the object illumination region 20, there is therefore a negligible variation in the thickness of the object illumination region 20 in the illumination beam path 2. As a result, in particular taking into account the dimensions of the objects to be studied, a constant thickness of the object illumination region and therefore a two-dimensional or planar structure thereof can be assumed to a first approximation.

Figure 5:
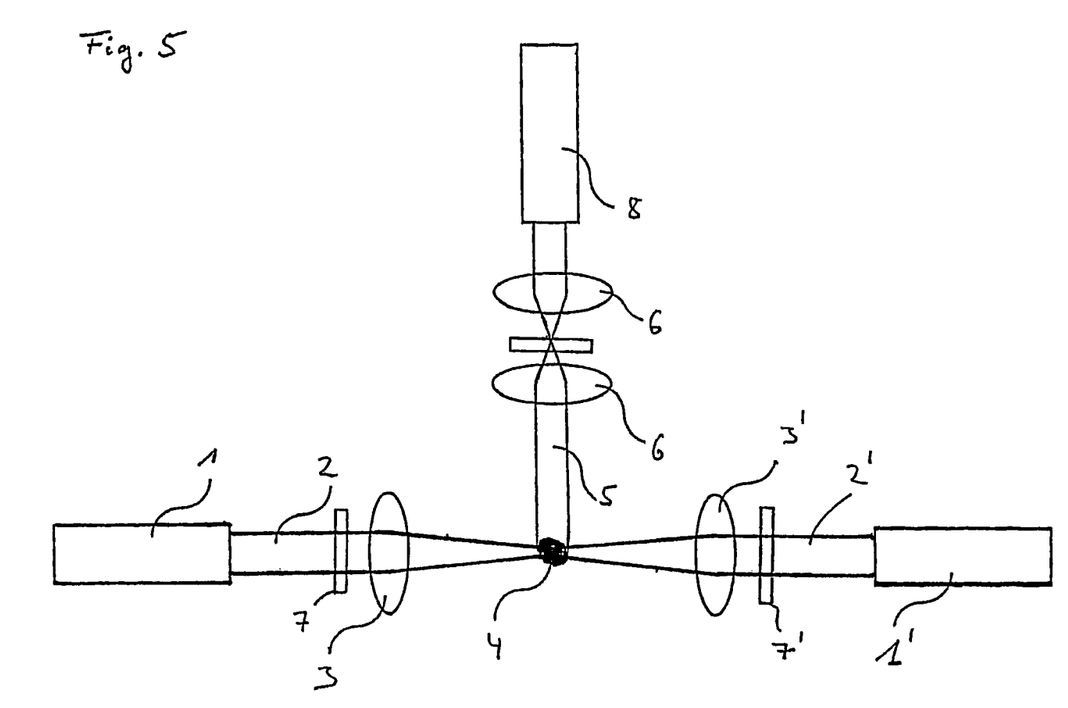
FIG. 5 shows the schematic representation of the beam path in another embodiment of the microscope according to the invention in which two illumination beam paths are provided.

FIG. 5 shows a modified configuration of the microscope 100 in which two of the illumination beam paths 2, 2' are provided. In the embodiment shown in FIG. 5, each of the two illumination beam paths 2, 2' have oppositely directed illumination directions but illumination axes corresponding to each other. Each of the two illumination beam paths 2, 2' has one of the cylindrical lenses 3, 3' with the optional filters 7, 7' and at least one of the light sources 1, 1'. In a variant of this embodiment, it is furthermore possible to provide more than just one light source 1, 1'. By superposition of the two object illumination regions 20 of the two illumination beam paths 2, 2'. The object illumination region 20 was explained above in more detail above with reference to FIGS. 3 and 4. The object illumination region 20 in this embodiment of the invention is a thin vertical light strip which is more homogeneous compared to the light strip in the embodiment represented in FIG. 1. The emitted light 5 is projected through the detection optics 6 onto the two-dimensional detector 8. This embodiment of the microscope according to the invention is particularly suitable for absorbent samples, for which it is not possible to illuminate the entire sample 4 with illumination from one side.

In this embodiment of the invention, it is possible to make the two illumination beam paths 2, 2', or their light beams, interfere deliberately by adjustment of the phase angle of the light beams along the two illumination paths 2, 2' with respect to each other. The two object illumination regions 20 of the two illumination beam paths 2, 2' mutually overlap. In this way, in the object illumination region 20 where the object or sample 4 to be studied is to be illuminated, it is possible to remove particular sections by destructive interference or highlight particular regions by constructive interference, so that the resolution of the overall system can be further improved.

Figure 2:
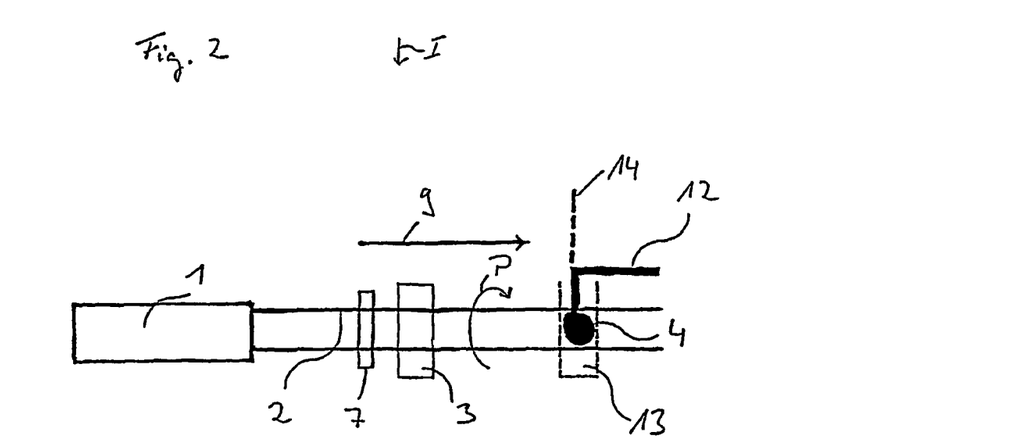
FIG. 2 shows the embodiment of FIG. 1 from the observation direction II in FIG. 1.
Figure 6:
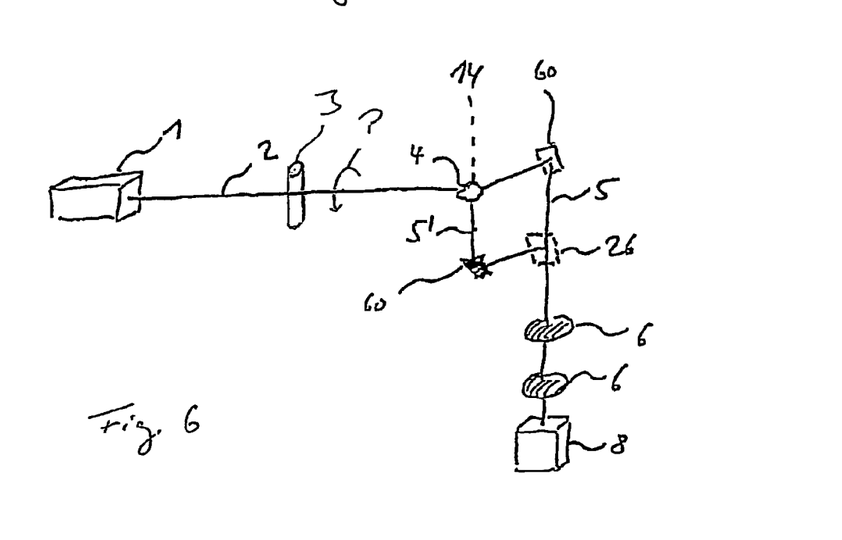
FIG. 6 shows another outline representation of a microscope according to the invention.

FIG. 6 illustration another embodiment of the microscope 100 according to the invention. The arrow P indicates that the cylindrical lens 3 shown therein can be rotated, for example through 90° about an illumination axis of the illumination beam path 2. The object illumination region 20 of this illumination beam path 2 is thereby also rotated so that, starting from the orientation shown in FIG. 2 in which it lies essentially in the plane of the drawing, it is rotated through 90° and is then perpendicular to the plane of the drawing. In this way, it is possible to view the object 4 to be studied from a different direction, i.e. the direction lying below this object 4 in the representation of FIG. 2. It is also possible to provide a further detection beam path 5' with which, in relation to the detection beam path 5 visible in FIG. 1, the object 4 to be studied can be viewed at an angle of 90° without this object 4 itself having been rotated.

In such an embodiment, for example by using mirrors 60 and a tilting mirror 26, it is possible to guide different ones of the detection beam paths 5, 5' selectively to the same detector 8, or the same optical system with objectives 6, according to the position of the tilting mirror 26. In accordance with the rotational position of the cylindrical lens 3, the tilting mirror 26 will then correspondingly be switched over. It is of course possible to provide two of the detection beam paths 5, 5' with a different one of the objective arrangement and detector, independently of each other and for example at an angle of 90° to each other. It is also possible to make at least one of these embodiments adjustable such that the one of the detection beam paths 5, 5' can be rotated together with the cylindrical lens 3 about the illumination axis of the illumination beam path 2 in FIG. 2. As a result an image can then be produced all around the object 4 to be studied by simultaneously rotating the cylindrical lens 3 and the detection beam path 5, 5' without moving the object 4 itself.

Figure 7:
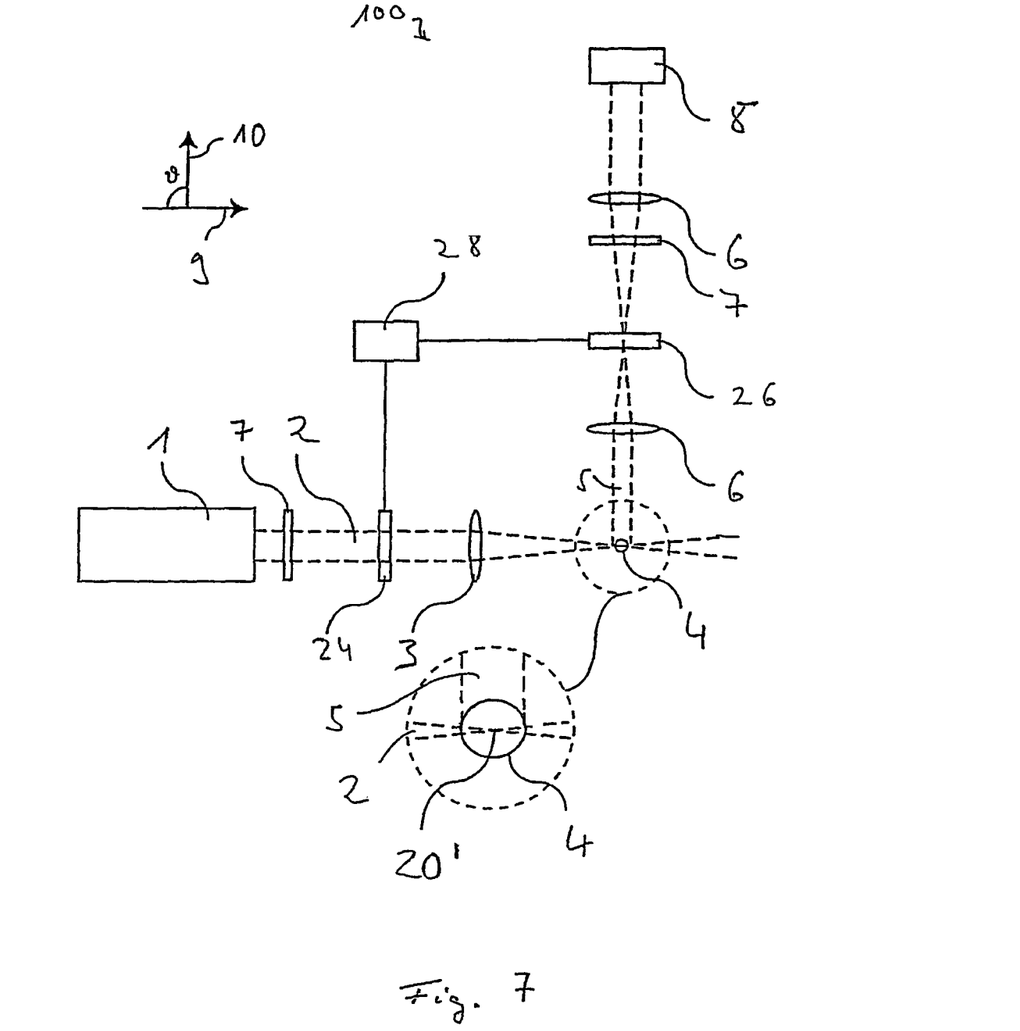
FIG. 7 shows a view corresponding to FIG. 1 of an alternatively configured microscope according to the invention.

An alternatively configured microscope 100 according to the invention is represented in FIG. 7. The basic structure, as well as the viewing mode, is the same as in FIG. 1 so that reference may generally be made to the comments above. There is again an illumination beam path 5, essentially provided by the light beam 2, which is focused by using an optical system in order to generate an object illumination region 20'. The lens 3 used here is no longer a cylindrical lens, but a lens which is rotationally symmetric with respect to the illumination axis 9 of the illumination beam path 5. This generates an object illumination region 20' which is likewise essentially rotationally symmetric and therefore, particularly in the region where the object 4 to be studied i.e. the sample is positioned, can be interpreted as a linear object illumination region or line-like object illumination region. The dimensions of this essentially rotationally symmetric linear object illumination region may, naturally depending on the focal length of the lens 3 or of the optical system being used, be in the range of 10-20 micrometers at the center while having a dimension in the range of 40-60 micrometers in the edge regions.

In this microscope 100 as shown in FIG. 7, therefore, a correspondingly linear region instead of a wafer-like or two-dimensional region of the sample 4 is lit when a sample 4 is positioned in the object illumination region 20'. The image of this linearly illuminated region as produced in the detection beam path 5 is projected via its optical system onto the detector 8, so that an optionally magnified line image is generated there. The detector 8 is constructed as a pixel detector and, in accordance with the linear image now produced, has more of a "one-dimensional" pixel arrangement. In this arrangement, the positioning of the pixels is such that a substantially larger number of the pixels will lie successively in the longitudinal direction of the linear image which is produced, than transversely thereto. The number of pixels in the longitudinal direction or transverse direction is preferably selected so that the linear image produced in the detection beam path 5 can be recorded fully by the detector 8 without having to move the detector 8. In the extreme case, it is even possible to provide a single row of pixels in the detector 8. Here, it should be borne in mind that with a decreasing width of such a pixel array and progressive transition to a single pixel line, the number of pixels present in such a linear arrangement can be increased and hence the resolution of the detector 8 can be enhanced correspondingly in this direction.

In order to be able to produce full images of the sample 4 with this high-resolution microscope 100 as represented in FIG. 7, even in view of the possible structure of the detector 8, a relative movement of this sample 4 with respect to the linear object illumination region 20' is produced according to the invention. There are in principle various ways of doing this. On the one hand, the sample 4 may be displaced orthogonally to the linear object illumination region and also orthogonally to the detection beam path 5, i.e. perpendicularly to the plane of the drawing in the representation of FIG. 7. In this way, linear regions of the sample 4 are successively illuminated by scanning, so that a full image of the sample 4 in a plane can be produced by combining the correspondingly recorded images. In order to generate a three-dimensional image, the sample 4 may furthermore be displaced in the direction of the detection beam path 5 or the detection direction 10, so that various planes of the sample 4 are moved through the focal plane of the illumination beam path 5.

In an alternative variant represented in FIG. 7, the sample 4 may be kept stationary while providing devices 24 and 26 both in the illumination beam path 2 and in the detection beam path 5 which facilitate displacement of these two beam paths 2, 5 in their region near the sample. For example, these devices 24, 26 may be beam deflection units which, for example, respectively contain a tiltable mirror. The two beam deflection units 24, 26 are operated by a control device 28 in order to match their movements to each other. The two beam deflection untis 24, 26 can be driven either by a small motor or by a galvanometer arrangement. This ensures that the region of the sample 4 currently being lit by the object illumination region 20' is always projected through the detection beam path 5 onto the detector 8. In this way it is possible for the sample 4, which otherwise cannot be moved perpendicularly to the plane of the drawing in FIG. 7, to be scanned in a plane. Here again, in order to obtain a three-dimensional representation, the sample 4 is then displaced again in the detection direction 10 in order to sample a plurality of planes in succession.

It is of course also possible to combine the two aforementioned ways of producing a relative movement between the sample 4, on the one hand, and the illumination beam paths, on the other hand, in which case it should be borne in mind that the movement of the illumination beam paths can be carried out faster than the movement of the sample.

With the system as represented in FIG. 7, it is thus possible to use high-resolution "one-dimensional" or elongated pixel arrays in the detector 8 in order to be able to produce correspondingly high-resolution images of the object illuminated regions of the sample 4. A further advantage of this "sampling" of the sample 4 is that the position of the object illumination region can be matched better to the field of view of the detection optics, i.e. the object illumination regions which are not intended to be imaged do not have to be sampled or illuminated at all, without causing any deterioration of the sampling or imaging of other regions of interest. This scan movement of the linear object illumination region with respect to the sample 4 to be studied furthermore gradually generates an illumination plane or a two-dimensional object illumination region which has a more homogeneous intensity in the direction of the relative movement than is the case with corresponding beam expansion in the systems described above, since the intensity profile in the object illumination region therein is also dependent on the intensity profile of the focused light beam. Higher intensities can also be achieved owing to the stronger focusing of the light. The laser power is therefore used more efficiently, which is advantageous particularly for weak fluorescence or multi-photon stimulation.

It should be pointed out that various aspects of the microscope according to the invention, for example the provision of different numbers of illumination beam paths and detection beam paths, or the relative positioning and phase adjustment thereof, the measures for moving an object by displacement or rotation or for moving the optical system, for example while the object is stationary, may of course be implemented irrespective of whether the object illumination region has a two-dimensional extent or is formed essentially as a band or linearly.

The invention relates to a microscope in which a layer of the sample is illuminated by a thin light strip 11 and the viewing takes place perpendicularly to the plane of the light strip. The thickness of the light strip 11 therefore essentially determines the depth of focus of the system. For the imaging, the object 4 is moved through the light strip 11 which is stationary with respect to the detector, and fluorescent and/or scattered light is recorded by a two-dimensional detector. Strongly absorbing or strongly scattering objects 4 are viewed from several spatial directions. The three-dimensional images which are recorded from each direction can subsequently be combined to form an image in which the data are weighted according to their resolution. The resolution of the combined image will then be dominated by the lateral resolution of the individual images.

A further embodiment of the invention is shown in FIGS. 8A and 8B which shows a sample 4 embedded in a cylindrically shaped agarose gel matrix 32 and suspended in a medium-filled chamber 30. As discussed above and indicated in FIGS. 8A and 8B, micro-positioning stages move and rotate the sample 4. FIGS. 8A and 8B illustrate the differences in this embodiment compared to the embodiment of FIG. 1. It should be noted that FIGS. 8A and 8B show the same embodiment of the invention in two different perspective directions.

The light source 1 is any laser suitable for illumination. In this embodiment of the invention, the sample 4 only required the Argon-ion 488 nm line. This is, however, not limiting of the invention. A grid 34 with a single spatial frequency is inserted into the illumination path 2. Different ones of the grids 34 with different spatial frequencies have been used (These are 10 lp/mm, 150 lp/mm precision Ronchi rulings 1"×3", Edmund Optics Inc.). The grids may be adapted to the detection system used and are not limiting to the invention. The grid 34 was shifted by a (not shown) micro-translation stage (model number M-111.1DG of Physik Instrumente GmbH & Co. KG, Karlsruhe, Germany). The grid 34 could also be shifted by the use of a galvanometer or a motor. A light beam from the light source 1 is passed through the cylindrical lens 3 (having f=50 mm and supplied by Melles Griot) to form the light sheet.

The fluorescence light in the detection beam path 5 was detected by an objective lens and a tube lens forming the detection optics 6, an emission filter 7 (RazorEdge LP 488 nm supplied by Semrock Inc.) and a CCD-camera 8 (ORCA ER supplied by Hamamatsu Photonics). Various ones of the objective lenses have been used (e.g. Achroplan 20×/0.50 W, Achroplan 40×/0.8 W, Carl Zeiss).

The sample 4 was kept in an aqueous environment which was adapted to the conditions required by the sample 4 (e.g. Phosphate Buffered Saline (PBS)) and which were required to investigate complete and intact ones of the samples 4. The sample 4 was inserted into a four-axis positioning device as discussed above. Three translational stages (M-232.17X) and one rotational stage (M-116.DG supplied by Physik Instrumente GmbH & Co. KG, Karlsruhe, Germany) provided four degrees of freedom for the sample 4.

FIGS. 9A-9D illustrate images of the front part of a *Drosophila melanogaster* trunk. FIG. 9A illustrates an image formed using the embodiment of FIG. 1. FIG. 9B illustrates an image formed from the embodiment of FIG. 8 with the grid 34.

FIG. 9C illustrates details of the fruit fly trunk (a) lamellum, (b) pseudotracheal sensilla, (c) left maxillary palpus, (d) rostral membrane. The details marked (e) can not be seen in FIG. 9A (i.e. embodiment of FIG. 1) but can be seen in FIG. 9B (i.e. second embodiment). FIG. 9D illustrate the normalised intensity values of two horizontal plots of images FIGS. 9A and 9B as indicated throught the section shown in FIG. 9C. The field of view of all images FIGS. 9A-9C is 364 μm×306 μm. The direction of illumination is from the top. FIGS. 9A and 9B are maximum projections of two stacks of images along the z-direction consisting of 181 planes with an axial pitch of 1.5 µm. A 20× objective lens was used in combination with the grid 34 having 10 lp/mm.

The sample 4 expresses Histone-GFP which was excited at a wavelength of 488 nm. Detection occurs above 494 nm. The fluorophore was expressed throughout the entire sample 4 in every cell at approximately the same level.

During the image recording process at least three images ($I_{0°}$, $I_{120°}$ and $I_{240°}$) were acquired. This is done by either passing the sample 4 through the illumination pattern or by moving the illumination pattern by moving the grid 34. The phase shift of the grid 34 between any two of the acquired images is $\Delta\phi = 2\pi/3 = 120°$. Every one of the images contains information that was present in the other ones of the images. Every one of the images also lacks information that was present in the other ones of the images. This process of recording three images was repeated for each plane in the stack of images. The recording time varied between 0.3 sec and 1 sec for an image triple (10-12 bits dynamic range, 1344×1024 pixels) and between 45 sec and 150 sec for complete stack of 150 image triples. Each image triple is then processed as follows.

$$I(z) = \|I_{0°} + I_{120°} \cdot e^{2\pi i/3} + I_{240°} \cdot e^{4\pi i/3}\| = \sqrt{((I_{0°} - I_{120°})^2 + (I_{120°} - I_{240°})^2 + (I_{240°} - I_{0°})^2)/2}$$

The resultant stack of images I(z) was used to generate the maximum intensity value projections shown in FIG. 9B. Apart from linear intensity adjustments no other image processing was applied. The axial pitch (adapted to the axial resolution) varies between 0.5 µm and 5 µm. Strictly, the pattern should be linearly sinusoidal but rectangular grids can also be used (as disclosed, for example, in M. J. Cole, J. Siegel, S. E. D. Web, R. Jones, K. Dowling, Mj. J. Dayel, D. Parsons-Karavassilis, P. M. W. French, M. J. Lever, L. O. D. Sucharov, M. A. A. Neil, R. Juskaitis, T. Wilson, J. Microsc. 203, 246-257 (2001) or in L. H. Schaefer, D. Schuster, J. Schaffer, J. Microsc. 216, 165-174 (2004).

Figure 8:
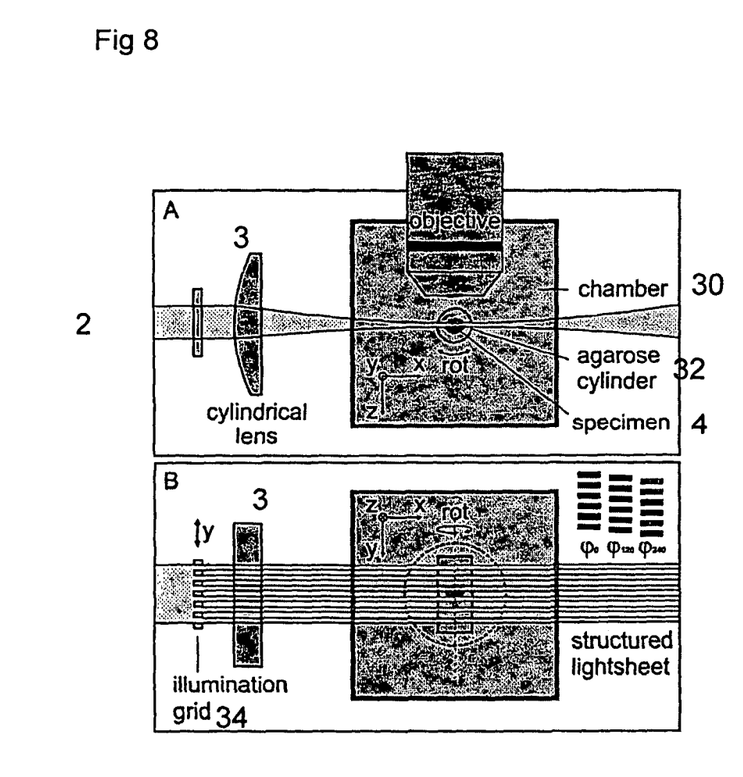
FIGS. 8A & 8B show a further embodiment of the invention incorporating a grid.
Figure 9:
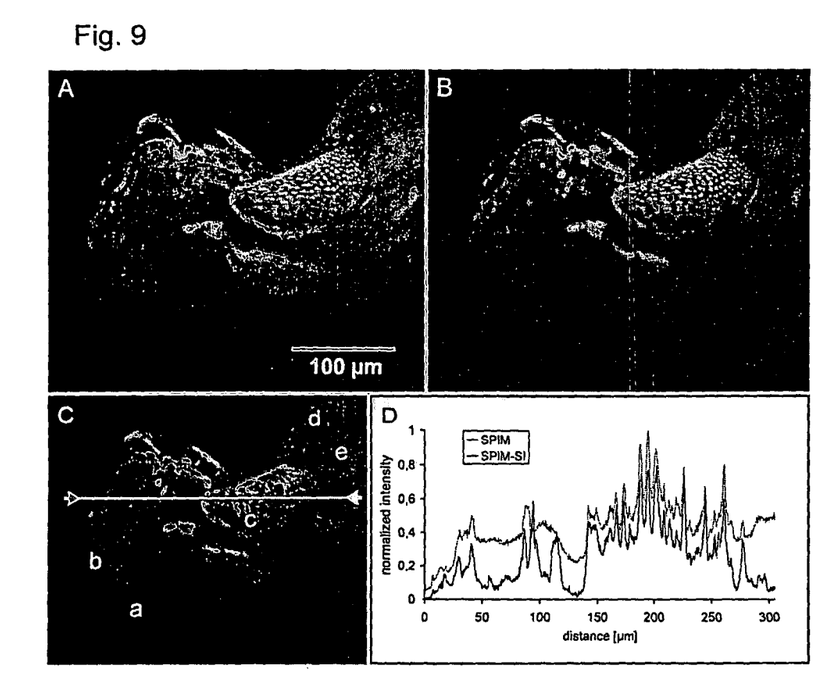
FIGS. 9A-9D show examples of images of front part of a Drosophila melanogaster trunk generated with two embodiments of the invention.

FIGS. 9A and 9B 2 show images recorded with a 20×/0.5 lens using the grid 34 with 10 lp/mm. Clearly, areas (a and b) in FIG. 9A that suffer from a strong background are much dimmer in FIG. 9B. Hence, features (d and e) that are hidden by out-of-focus background contribution are enhanced. Most features in area (d) are not visible in FIG. 9A but clearly visible in FIG. 9B. The intensity plot comparing values derived from FIG. 9A and FIG. 9B showed that the further embodiment of the invention illustrated in FIG. 9 reduced the background and improved the lateral resolution. The line representing the embodiment of FIG. 8 is steeper and reveals details not visible along the line representing the embodiment of FIG. 1.

In an alternate embodiment of the invention a light mirror is used instead of the cylindrical lens 3. The laser beam from the light source 1 is shone onto the light mirror which is then moved in a plane to form a light plane.

Various embodiments which incorporate the teachings of the present invention have been shown and described in detail in this specification. Those skilled in the art can readily devise many other embodiments that still utilize these teachings.

The invention claimed is:

1. A microscope having at least one illumination beam path and at least one detection beam path, wherein
    the at least one each illumination beam path is provided with a focusing arrangement for producing a two-dimensional object illumination pattern which extends in the direction of an illumination axis of the at least one illumination beam path and in a transverse direction substantially transverse to the illumination axis,
    a detection direction of the at least one detection beam path is substantially orthogonal to the two-dimensional object illumination pattern, and
    a mobile arrangement is provided for producing a relative movement between the two-dimensional object illumination pattern and an object to be studied, wherein the two-dimensional object illumination pattern is a set of substantially parallel light stripes.

2. The microscope as claimed in claim 1, wherein the set of substantially parallel light stripes can be shifted with respect to the object to be studied.

3. The microscope as claimed in claim 1, further comprising a grid for generating the set of parallel light stripes from a single one of the light source.

4. The microscope as claimed in claim 1, wherein the mobile arrangement can produce a rotational movement of the object.

5. The microscope as claimed in claim 1, wherein the mobile arrangement can produce a displacement movement of the object.

6. The microscope as claimed in claim 1, wherein the mobile arrangement is designed to move the object while the two-dimensional object illumination pattern is essentially stationary.

7. The microscope as claimed in claim 1, wherein the mobile arrangement is designed to move the two-dimensional object illumination pattern while the object is essentially stationary.

8. The microscope as claimed in claim 1, wherein the at least one illumination beam path has a cylindrical lens for focusing the illumination light.

9. The microscope as claimed in claim 8, wherein the cylindrical lens is movable with respect to the illumination axis.

10. The microscope as claimed in claim 9, wherein the cylindrical lens can be rotated about the illumination axis.

11. The microscope as claimed in claim 9, wherein the cylindrical lens can be displaced in the direction of the illumination axis.

12. The microscope as claimed in claim 9, wherein the cylindrical lens can be displaced in the direction of the cylinder axis.

13. The microscope as claimed in claim 9, wherein the cylindrical lens can be tilted via the cylinder axis with respect to the illumination axis.

14. The microscope as claimed in claim 9, wherein the movement of the cylindrical lens is a high-frequency movement.

15. The microscope as claimed in claim 1, wherein the mobile arrangement comprises at least one light mirror and the focussing arrangement.

16. The microscope as claimed in claim 15, wherein the at least one light mirror is driven by a galvanometer.

17. The microscope as claimed in claim 16, wherein the at least one light mirror is driven by a motor.

18. The microscope as claimed in claim 15, wherein the mobile arrangement and the focussing arrangement comprise at least two light mirrors.

19. The microscope as claimed in claim 15, wherein the illumination light of the two illumination beam paths has a constant, adjustable phase.

20. The microscope as claimed in claim 1, wherein scattered light or fluorescent light of one or more wavelengths is used.

21. The microscope as claimed in claim 20, wherein at least two illumination beam paths with essentially opposite illumination directions are provided for producing at least locally overlapping two-dimensional object illumination patterns.

22. The microscope as claimed in claim 20, wherein the illumination light of the two illumination beam paths interferes at least locally in the direction of the illumination axis in the region of the two-dimensional object illumination pattern.

23. The microscope as claimed in claim 1, wherein the light source is a lamp or a laser, providing light of one or more wavelengths.

24. The microscope as claimed in claim 1, wherein the object is held by a holder in a sample chamber, in which the object can be rotated about an axis corresponding essentially to the gravitational direction and can be moved along at least one direction.

25. The microscope as claimed in claim 1, wherein the at least one detection beam path has a detector, the detector being laterally movable with respect to the detection direction of the at least one detection beam path.

26. The microscope as claimed in claim 1, wherein the at least one detection beam path can be adapted so that the detection direction is substantially orthogonal to the two-dimensional object illumination pattern when the object illumination region is shifted.

27. The microscope as claimed in claim 1, wherein each one of the substantially parallel light stripes extends in the direction of the illumination axis and in the transverse direction, and wherein each one of the substantially parallel light stripes is displaced with respect to any other of the substantially parallel light stripes in the transverse direction of the two-dimensional object illumination pattern.

\* \* \* \* \*